United States Patent [19]
Bryant et al.

[11] Patent Number: 5,489,569
[45] Date of Patent: Feb. 6, 1996

[54] COMPOSITION AND METHOD FOR INCREASING THE EFFECTIVENESS OF PESTICIDES

[75] Inventors: Stephen D. Bryant, Bartlett; James C. Lee, Memphis, both of Tenn.; M. Sheldon Ellis, Ft. Collins, Colo.

[73] Assignee: Buckman Laboratories International, Inc., Memphis, Tenn.

[21] Appl. No.: 383,677

[22] Filed: Feb. 1, 1995

Related U.S. Application Data

[63] Continuation of Ser. No. 73,525, Jun. 9, 1993, abandoned, which is a continuation-in-part of Ser. No. 990,078, Dec. 14, 1992, abandoned.

[51] Int. Cl.$^6$ .......................... A01N 37/18; C07C 235/04
[52] U.S. Cl. ............................ 504/166; 504/339; 554/35
[58] Field of Search ................................. 504/166, 339; 554/35

[56] References Cited

U.S. PATENT DOCUMENTS

| | | | |
|---|---|---|---|
| 2,576,080 | 11/1951 | Tischler et al. | 504/166 |
| 3,760,042 | 9/1973 | Beriger et al. | 558/183 |
| 3,874,870 | 4/1975 | Green et al. | 71/67 |
| 3,931,319 | 1/1976 | Green et al. | 260/567.6 |
| 4,027,020 | 5/1977 | Green et al. | 424/248.56 |
| 4,089,977 | 5/1978 | Green et al. | 424/329 |
| 4,111,679 | 9/1978 | Shair et al. | 71/67 |
| 4,506,081 | 3/1985 | Fenyes et al. | 548/523 |
| 4,581,058 | 4/1986 | Fenyes et al. | 71/67 |
| 5,006,159 | 4/1991 | Markley et al. | 504/344 |
| 5,213,805 | 5/1993 | Wallach et al. | 424/450 |

FOREIGN PATENT DOCUMENTS

| | | |
|---|---|---|
| 0231765 | 1/1987 | European Pat. Off. . |
| 150544 | 1/1932 | Switzerland . |
| 92/19104 | 11/1992 | WIPO . |

OTHER PUBLICATIONS

Ash et al., "Chemical Tradename Dictionary," NY, VCH Publishers, 1993, p. 165.
CA62:453b "Aminohydroxy Fatty Amides" Rogier, E. R. (1965).
Material Safety Data Sheet for Accelerate®, Form 4627, Rev. (Apr. 1989), Pennwalt Corporation, Agchem Division, Three Parkway, Philadelphia Pa. 19102.
Material Safety Data Sheet for Des–i–cate®, Form 4627, Rev. (Apr. 1989) Pennwalt Corporation, Agchem Division, Three Parkway, Philadelphia, Pa. 19102.
Material Safety Data Sheet for Bulab 6050, Revision Data (Dec. 4, 1991), Buckman Laboratories, Inc., 1256 North McLean Boulevard, Memphis TN 38108.
Crowley, "A Pesticide Primer," Hazelton Wisconsin Agrichemical Newsletter, 1:1–6 (Oct. 1990).
"Product Category Index," in Crop Protection Chemicals Reference, 6th ed., Chemical and Pharmaceutical Press, New York (1990), pp. 17–20 of "Product Category Index".
"Busperse®47," Document No. A146W (Oct. 1992), Buckman Laboratories, Inc., 1256 North McLean Boulevard, Memphis, TN 38108 (1992). (1 page).
"Busperse®47—Penetrant, Dispersant, and Fatliquoring Aid for the Leather Industry," Document No. D9W, Buckman Laboratories, Inc., 1256 North McLean Boulevard, Memphis TN 38108 (1991). (1 page).
"Busperse®47—Viscosity Depressant for High Solids Coatings", Document No. B30W (Aug. 1992), Buckman Laboratories, Inc., 1256 North McLean Boulevard, Memphis TN 38108 (1992). (1 page).
"Buseperse®47—For Increasing the Cleaning Power of Boilout Solutions Used in Sugar Mills," Document No. S5W (Mar. 1993), Buckman Laboratories, Inc., 1256 North McLean Boulevard, Memphis, TN 38108 (1991). (2 pages).

*Primary Examiner*—Allen J. Robinson
*Assistant Examiner*—Mary C. Cebulak
*Attorney, Agent, or Firm*—Finnegan, Henderson, Farabow, Garrett & Dunner

[57] ABSTRACT

Pesticidal and fertilizer compositions containing at least one compound of formula I $$R_3C(O)-N(R_1)(R_2) \qquad (I)$$

wherein $R_1$ is hydrogen or a substituted or unsubstituted $C_1$–$C_6$ alkyl group; $R_2$ is hydrogen or a substituted or unsubstituted $C_1$–$C_6$ alkyl group; and $R_3C(O)$— is a substituted or unsubstituted fatty acid residue of 8 to 22 carbon atoms are provided. A method of increasing the effectiveness of a pesticide which comprises applying a pesticide and an amount of a compound of formula I effective to increase the pesticidal activity of the pesticide is also provided. A method for increasing the effectiveness of a fertilizer which comprises applying to a plant in need thereof a fertilizer and an amount of a compound of formula I effective to increase the fertilizing activity of the fertilizer is also described.

10 Claims, No Drawings

COMPOSITION AND METHOD FOR INCREASING THE EFFECTIVENESS OF PESTICIDES

This application is a continuation of application Ser. No. 08/073,525 filed Jun. 9, 1993, now abandoned, which is a continuation-in-part of application Ser. No. 07/990,078 filed Dec. 14, 1992, abandoned, the contents of which are hereby incorporated by reference.

The present invention utilizes at least one compound of formula I, defined below, or a modified vegetable oil, defined below, or at least one ionene polymer to increase the effectiveness of a pesticide. The invention thus relates to pesticidal compositions, as well as concentrated pesticidal formulations. The invention also relates to a method for increasing the effectiveness of a pesticide by applying at least one compound of formula I, defined below, or a modified vegetable oil, defined below, or at least one ionene polymer in conjunction with a pesticide. In a preferred embodiment, the pesticide is a herbicide capable of foliar application.

Organic chemicals registered and applied as pesticides, especially herbicides, have achieved widespread use throughout the world in the production of agronomic and horticultural crops. A common example of the use of selected herbicidal products is for the prevention or eradication of at least one specific weed. Other common examples of the use of selected pesticidal products are for the prevention or eradication of an insect or fungus. A general discussion of pesticides is provided in Crowley, "A Pesticide Primer," *Hazleton Wisconsin Agricultural Newsletter*, 1:1–6 (1990).

The present invention is useful for increasing the effectiveness of many types of pesticides. A pesticide is any substance or mixture of substances that is useful for preventing, destroying, repelling, or mitigating any pest, or used as a plant regulator, defoliant, or desiccant. Examples of pesticides are fungicides, herbicides, desiccants, plant growth regulators, seed protectants, defoliants, insecticides, insect growth regulators, miticides, and nematicides. The present invention is also useful for increasing the effectiveness of fertilizers, especially fertilizers capable of foliar application.

The basis of the enhancement of the effectiveness of pesticides and fertilizers provided by the present invention is believed to be the penetrating and dispersing action of the compound of formula I, defined below. Specifically, it is believed that the compound of formula I assists in overcoming the principal impediment to pesticidal activity, the penetration of the pesticide through the object or target's protective surface. For example, the compound of formula I is believed to assist the penetration of herbicide through the waxy cuticle of a leaf surface. The compound of formula I enhances the penetration and, thus, the pesticidal activity of all categories of pesticides. In addition, the compound of formula I enhances the penetration and activity of fertilizers, especially fertilizers capable of foliar application. In the discussion which follows, the invention will be described in terms of a preferred embodiment of a pesticide, a herbicide, but the invention is not limited to herbicides.

A common example of a pesticide is a herbicide. A herbicide may be used for the prevention or eradication of at least one specific weed. Other types of herbicides, such as harvest aids or those used for vegetation management, provide an action different from killing a specific weed.

A non-crop example of vegetation management is the use of a growth inhibitor to suppress the growth of turfgrass. This type of growth inhibitor has been utilized along highway rights-of-way and on golf courses. An example of such a growth inhibitor is Embark® product, manufactured by 3M Company, St. Paul, Minn.

There are numerous crop applications of herbicides known as harvest aids. One example is the use of a particular product as a cotton defoliant. Examples include DROPP® product, manufactured by NOR-AM Chemical Co., Wilmington, Del., and DEF® product, manufactured by Miles, Inc., Kansas City, Miss. The chemical is sprayed on the mature plants prior to harvest. The leaves then fall off (abscise) and leave only the cotton bolls attached to the stem structure. The defoliated plants are easier to pick, and less trash is introduced into the cotton fiber.

A second example is the desiccation of potato vines prior to harvest. This facilitates mechanical harvesting of the underground tubers and enhances "skin set" on the tuber which prevents stem-end rot. Desiccants are also used as harvest aids in cotton production.

Endothall is the common name for (7-oxabicyclo[2,2,1] heptane-2,3-dicarboxylic acid). Endothall is the active ingredient contained in Des-i-cate® and Accelerate® agricultural products (Atochem North America, Philadelphia, Pa.). Accelerate® and Des-i-cate® products are formulations both of which contain mixed mono and di (N,N-dimethylalkylamine) salts of endothall, which have an average molecular formula of $C_{14}H_{31}N$. Accelerate® and Des-i-cate® products contain 5.5 weight percent of endothall. Accelerate® product is registered as a harvest aid for cotton production. Accelerate® product is applied by spraying on cotton plants one to two weeks prior to harvest. This kills the leaves and facilitates the mechanical harvesting of the cotton bolls. Des-i-cate® product is registered for use as a potato vine killer and as a harvest aid for alfalfa and clover.

An alternative formulation of endothall is marketed as an algicide/herbicide for industrial water treatment as Hydrothol® 191 product (Atochem North America, Philadelphia, Pa.) and Bulab® 6050 product (Buckman Laboratories, Memphis, Tenn.). Bulab® 6050 and Hydrothol® 191 products are solutions of 53 weight percent mono(N,N-dimethylalkylamine) salts of endothall and 47 weight percent inert ingredients. The mono(N,N-dimethylalkylamine) salts are derived from coconut oil. Bulab® 6050 and Hydrothol® 191 products Contain 23 weight percent of endothall.

Potato growers often have experienced performance deficiencies with prior art products. In fields with dense growth, insufficient vine kill may be a problem. This leads to stem regrowth which complicates harvesting and results in poor skin set. Sequential applications seven to ten days apart are an option, provided that the grower can afford the additional cost.

The effectiveness of a herbicide in any of the previously discussed applications is dependent on the quantity applied, the method of application, and the environmental conditions during the application. The objective of the grower or herbicide applicator is to achieve a desired result with the least amount of chemical and at the lowest cost. Furthermore, in spite of the international concern about pesticides and herbicides, the amount of pesticides and herbicides being used continues to grow. When applying any pesticide, as in the case of a herbicide specifically, the goal is to use the least amount of pesticide to achieve the desired result.

Accordingly, the invention is directed to a composition which comprises a pesticide and a compound which enhances the effectiveness of the pesticide and, thus, can make possible use of lower amounts of pesticide. The invention also provides a method for increasing the effectiveness of a pesticide by applying compounds capable of achieving the desired effect in conjunction with the pesticide.

The invention provides improved performance of the pesticide which can result, desirably, in the use of less pesticide. The use of less pesticide provides both economic and environmental benefits.

In one embodiment, the invention relates to a pesticidal composition comprising at least one pesticide and at least one compound of formula I

wherein $R_1$ is hydrogen or a substituted or unsubstituted $C_1$–$C_6$ alkyl group; $R_2$ is hydrogen or a substituted or unsubstituted $C_1$–$C_6$ alkyl group; and $R_3C(O)$— is a substituted or unsubstituted fatty acid residue of 8 to 22 carbon atoms.

Another embodiment of the invention provides a pesticidal composition comprising at least one pesticide and a modified vegetable oil comprising at least one compound of formula I, defined above.

A third embodiment of the invention provides a method of increasing the effectiveness of a pesticide which comprises applying to an object or target in need thereof an amount of a compound of formula I, defined above, effective to increase the pesticidal activity of the pesticide.

The invention, in a further embodiment, provides a concentrated pesticidal formulation comprising (a) at least one pesticide; (b) at least one water-soluble coupling agent; and (c) at least one compound of formula I, defined above.

In another embodiment, the invention provides a concentrated pesticidal formulation comprising (a) at least one pesticide; (b) at least one water-soluble coupling agent; and (c) a modified vegetable oil comprising at least one compound of formula I, defined above.

In another embodiment, the invention provides a concentrated pesticidal formulation comprising (a) at least one pesticide; (b) at least one coupling agent selected from propylene glycol and dipropylene glycol; and (c) a modified vegetable oil selected from modified palm, soybean, and tall oil, in which the modified vegetable oil comprises at least one compound of formula I, defined above.

One embodiment of the invention provides a pesticidal composition comprising a pesticide and an ionene polymer.

Another embodiment of the invention provides a fertilizer composition comprising at least one fertilizer and at least one compound of formula I, defined above.

The invention provides a composition and method for enhancing the effectiveness of pesticides, especially herbicides, and fertilizers. The composition and method may be used for desiccating crops prior to harvest. Additional objects and advantages of this invention will be set forth in the description which follows, and in part will be apparent from the description, or may be learned by the practice of this invention.

As a first embodiment, the invention provides a pesticidal composition comprising at least one pesticide capable of foliar application and at least one compound of formula I

wherein $R_1$ is hydrogen or a substituted or unsubstituted $C_1$–$C_6$ alkyl group; $R_2$ is hydrogen or a substituted or unsubstituted $C_1$–$C_6$ alkyl group; and $R_3C(O)$— is a substituted or unsubstituted fatty acid residue of 8 to 22 carbon atoms. In a preferred embodiment, the pesticidal composition is a herbicidal composition.

When $R_1$ or $R_2$ is a substituted or unsubstituted $C_1$–$C_6$ alkyl group, the $C_1$–$C_6$ alkyl group can, of course, be non-cyclic or, for $C_3$–$C_6$ alkyl, can be cyclic, e.g., cyclohexyl. However, the $C_1$–$C_6$ alkyl group is preferably branched or straight chain and/or saturated or unsaturated. More preferably, $R_1$ and $R_2$ are independently selected from methyl, ethyl, and propyl. In a further preferred embodiment, $R_1$ and $R_2$ are methyl.

The substituted fatty acid residue $R_3C(O)$— may contain, in addition to the fatty acid residue of 8 to 22 carbon atoms, additional alkyl groups substituted onto the residue, which alkyl groups may be branched or straight chain and/or saturated or unsaturated. Preferred pesticidal compositions are those in which $R_3C(O)$— is a substituted or unsubstituted fatty acid residue of 8 to 18 carbon atoms or those in which $R_3C(O)$— is a substituted or unsubstituted fatty acid residue of 12 to 18 carbon atoms. A fatty acid residue is a saturated or unsaturated chain of alkyl groups attached to a carbonyl group in which the chain of alkyl groups corresponds to the alkyl structure of a fatty acid. For example, the fatty acid residue of oleic acid, $CH_3(CH_2)_7CH{:}CH(CH_2)_7COOH$, is $CH_3(CH_2)_7CH{:}CH(CH_2)_7C(O)$—.

The pesticide in the pesticidal composition may be any pesticide used to prevent, destroy, repel, or mitigate any pest, or used as a plant regulator, defoliant, or desiccant. Pesticides are often classified according to their use. The pesticide may be, for example, a desiccant, fungicide, herbicide, plant growth regulator, seed protectant, defoliant, insecticide, insect growth regulator, miticide, or nematicide, or a salt of any of these pesticides.

In a preferred embodiment, the pesticide is a desiccant or a salt thereof. The desiccant may be selected from endothall, tributyl phosphotrithioate, ametyryn, and paraquat, or a salt of any of these desiccants. Desiccants such as those listed are commercially available and often used in agriculture as defoliants and herbicides. Suitable desiccants include "DEF 6" (Mobay), "EVIK 80W" (Ciba-Geigy), and "GRAMOXONE SUPER" (ICI) products.

In another embodiment, the pesticide is a fungicide or a salt thereof. The fungicide may be selected from any commercially available fungicide such as metalaxyl, triadimefon, benomyl, chlorothalonil, and propiconazole, or a salt of any of these fungicides. Suitable fungicides include "APRON 25W" (Ciba-Geigy), "BAYLETON 50% DF" (Mobay), "BENLATE" (DuPont), "BRAVO 500" (Fermenta), and "TILT" (Ciba-Geigy) products.

In one embodiment, the pesticide is a herbicide or a salt thereof. The herbicide may be selected from any commercially available herbicide such as endothall, atrazine, metribuzin, a salt of any of these herbicides. Suitable herbicides include Bulab® 6050 product (Buckman Laboratories), and "ATRAZINE 4L" (DuPont), "CANOPY" (DuPont), "COMMAND 4EC" (FMC), "FUSILADE 2000" (ICI), and "SCEPTER" (Cyanamid) products.

In an embodiment, the pesticide is a plant growth regulator or a salt thereof. The plant growth regulator may be selected from any commercially available plant growth regulator such as chlormequat chloride, 2-chloroethyl phosphonic acid, tributyl phosphonotrithioate, mepiquat chloride, and maleic hydrazide, or a salt of any of these plant growth regulators. Suitable plant growth regulators include "CYCOCEL" (Cyanamid), "ETHREL PLANT REGULATOR" (Rhone-Poulenc), "FOLEX 6EC" (Rhone-Poulenc), "PIX" (BASF), and "ROYAL MH-30" (Uniroyal Chemical) products.

In another embodiment, the pesticide is a seed protectant or a salt thereof. The seed protectant may be any commercially available seed protectant. In a further embodiment, the pesticide is a defoliant or a salt thereof. The defoliant may be any commercially available defoliant such as thidiazuron or a salt thereof. A suitable defoliant is "DROPP® 50WP" product (NOR-AM).

The pesticide may be an insecticide or a salt thereof. The insecticide may be selected from any commercially available insecticide such as permethrin, *Bacillus thuringiensis*, chloropyrifos, and carbaryl, or a salt of any of these insecticides. Suitable insecticides include "AMBUSH" (ICI), "DIPEL 4L" (Abbott), "LORSBAN 4E" (Dow), "POUNCE 3.2 EC" (FMC), and "SEVIN 80S" (Rhone-Poulenc) products.

The pesticide may be an insect growth regulator or a salt thereof. The insect growth regulator may be any commercially available insect growth regulator such as N-[(4-chlorophenyl)aminocarbonyl]-2,6-difluorobenzamide or a salt thereof. A suitable insect growth regulator is "DIMILIN 25W" product (Uniroyal Chemical).

The pesticide may also preferably be a miticide or a salt thereof. The miticide may be selected from any commercially available miticide such as propargite, dimethoate, 2,4-dinitro-6-octyl-phenylcrotonate, and oxamyl, or a salt of any of these miticides. Suitable miticides include "COMITE" (Uniroyal Chemical), "CYGON 400" (Cyanamid), "KARATHANE LC" (Rohm and Haas), "OMITE 30W" (Uniroyal Chemical), and "VYDATE L" (DuPont) products.

The pesticide may be a nematicide or a salt thereof. The nematicide may be selected from any commercially available nematicide such as terbufos, carbofuran, ethoprop, ethyl 3-methyl-4-(methylthio)phenyl (1-methylethyl)-phosphoroamidate, or a salt of any of these nematicides. Suitable nematicides include "COUNTER" (Cyanamid), "FURADAN 4F" (FMC), "MOCAP EC" (Rhone-Poulenc), "NEMACUR 3" (Mobay), and "VYDATE L" (DuPont) products.

A pesticide capable of foliar application is any pesticide that can be used by applying it to an exposed portion of a plant. Likewise, a herbicide capable of foliar application is any herbicide that can be used by applying it to an exposed portion of a plant. The herbicide capable of foliar application may be selected from any commercially available herbicide such as endothall, acifluoren, dicamba, diclofop methyl, sethoxydim, glyphosate, paraquat, and tebuthiuron, or may be selected from a salt of any of these herbicides. Suitable herbicides include Des-i-cate® product (Atochem North America) and "GRAMOXONE SUPER" product (ICI). In a preferred embodiment, the herbicide is endothall or a salt thereof. The weight ratio of endothall:compound of formula I may be from 1:2 to 2:1.

A pesticidal composition according to the invention may further comprise water.

The fatty acid residue, $R_3C(O)$—, of compound I of the pesticidal composition, defined above, may be a substituted or unsubstituted residue of a fatty acid which occurs in a vegetable oil. The vegetable oil may be selected from tall oil, palm oil, soybean oil, cottonseed oil, coconut oil, corn oil, peanut oil, canola oil, safflower oil, sunflower oil, babassu oil, castor oil, linseed oil, olive oil, and tung oil. In a preferred embodiment, the vegetable oil may be selected from tall oil, palm oil, and soybean oil.

The invention also encompasses a pesticidal composition, defined above, in which the compound of formula I is present in a modified vegetable oil which forms part of the pesticidal composition. In a preferred embodiment, the pesticidal composition is a herbicidal composition. A modified vegetable oil is a vegetable oil in which the component fatty acids of the natural vegetable oil have been modified to have the structure of compound I defined above. Preferably, at least 50 percent of the fatty acids present in the modified vegetable oil have been modified to have the structure of compound I defined above. More preferably, at least 95 percent of the fatty acids present in the modified vegetable oil have been so modified. The vegetable oils contemplated to be modified to have the structure of compound I are those listed above. In a preferred embodiment, the vegetable oil may be selected from tall oil, palm oil, and soybean oil.

The invention also provides a pesticidal composition comprising at least one pesticide and a modified vegetable oil, defined above, comprising at least one compound of formula I, defined above. The preferred embodiments of the compound of formula I are the same as above. In a preferred embodiment, the pesticidal composition is a herbicidal composition, especially a herbicidal composition capable of foliar application. In a further preferred embodiment, the herbicide is endothall or a salt thereof, the modified vegetable oil is selected from tall oil, palm oil, and soybean oil, and $R_1$ and $R_2$ are methyl.

The invention provides a method of increasing the effectiveness of a pesticide which comprises applying to an object or target a pesticide and an amount of a compound of formula I effective to increase the pesticidal activity of the pesticide. The object or target may be, for example, a street, sidewalk, highway, railroad right-of-way, fencepost, plant, insect, mite, or nematode. Other targets and hosts include lakes, ponds, irrigation and drainage canals, landfills, wood, leather, soil, and painted surfaces. When the target is a plant, the plant may be an agricultural crop, horticultural or ornamental specimens, or turfgrass, e.g., grass on a golf course.

The definition and preferred embodiments of the compound of formula I as employed in this method are the same as above. In a preferred embodiment, the pesticide is a herbicide, especially a herbicide capable of foliar application. The pesticide or herbicide capable of foliar application is preferably applied, along with the compound of formula I, to an exposed portion of the object or target, e.g., a plant. The compound of formula I may be present in a modified vegetable oil. The compound of formula I and the pesticide may be applied simultaneously or separately. In a preferred embodiment, the compound of formula I and the pesticide are applied simultaneously in the form of an aqueous solution which comprises both the compound of formula I and the pesticide.

In a preferred embodiment, the pesticide employed in the method described above may be endothall or a salt thereof. The plant may be, for example, selected from potato vines, cotton plants, hops, alfalfa, and clover. In a preferred embodiment, the plant is selected from potato vines and cotton plants.

The invention also provides a concentrated pesticidal formulation comprising (a) at least one pesticide; (b) at least one water-soluble coupling agent; and (c) at least one compound of formula I, defined above. The preferred embodiments of the compound of formula I are the same as above. In a preferred embodiment, the pesticide is a herbicide capable of foliar application. The concentrated pesticidal formulation may comprise components (a) and (c) in an amount to be pesticidally effective upon dilution, and component (b) in an amount effective to increase the solubility of component (c) in the concentrated formulation. The concentrated pesticidal formulation may comprise component (b) in an amount effective to increase the solubility of component (c) upon dilution of the concentrated pesticidal formulation with water. The concentrated pesticidal formulation may also contain water.

In a preferred embodiment of the concentrated pesticidal formulation described above, the pesticide is endothall or a salt thereof. The compound of formula I may be present in a modified vegetable oil which forms part of the concentrated pesticidal formulation. The modified vegetable oil is preferably modified palm oil, soybean oil, or tall oil.

The coupling agent may be a substituted or unsubstituted $C_1$–$C_6$ alcohol or a substituted or unsubstituted $C_2$–$C_6$ glycol. The coupling agent may be ethanol, propanol, butylene glycol, propylene glycol, dipropylene glycol, or hexylene glycol. Preferred coupling agents are propylene glycol and dipropylene glycol. The coupling agent can stabilize the formulation, i.e., it can prevent the components of the formulation from separating.

The invention also provides a concentrated pesticidal formulation comprising (a) at least one pesticide; (b) at least one water-soluble coupling agent; and (c) a modified vegetable oil comprising at least one compound of formula I. The definition and preferred embodiments of the compound of formula I are the same as above. In a preferred embodiment, the pesticide is a herbicide capable of foliar application. The concentrated pesticidal formulation preferably comprises components (a) and (c) in an amount to be pesticidally effective upon dilution and component (b) in an amount effective to increase the solubility of component (c) in the concentrated formulation.

The invention encompasses a concentrated pesticidal formulation comprising (a) at least one pesticide; (b) at least one coupling agent selected from propylene glycol and dipropylene glycol; and (c) a modified vegetable oil selected from modified palm, soybean, and tall oil. Components (a) and (c) are preferably present in an amount to be pesticidally effective upon dilution, and component (b) is present in an amount effective to increase the solubility of component (c) in the concentrated formulation. The modified vegetable oil preferably comprises at least one compound of formula I, as defined above, where $R_1$ is methyl and $R_2$ is methyl.

In a preferred embodiment of the concentrated pesticidal composition, the endothall or a salt thereof is the mono(N,N-dimethylalkylamine) salt of endothall. The mono(N,N-dimethylalkylamine) salt may be derived from coconut oil. In another preferred embodiment of the concentrated pesticidal composition, the modified vegetable oil is modified palm oil and the coupling agent is propylene glycol. In a further preferred embodiment of the concentrated pesticidal composition, the modified vegetable oil is modified soybean oil and the coupling agent is propylene glycol. In another preferred embodiment of the concentrated pesticidal composition, the modified vegetable oil is modified tall oil and the coupling agent is dipropylene glycol.

The invention also encompasses a pesticidal composition comprising at least one pesticide and at least one ionene polymer. In a preferred embodiment, the pesticide is a herbicide capable of foliar application.

Ionene polymers are cationic polymers containing quaternary nitrogens in the polymer backbone. U.S. Pat. Nos. 3,874,870; 3,931,319; 4,027,020; 4,089,977; 4,506,081; 4,581,058; and 4,111,679 give various examples of these polymers. The disclosures of these patents are incorporated specifically by reference herein.

In a preferred embodiment, the ionene polymer is poly[oxyethylene(dimethyliminio)ethylene-(dimethyliminio)ethylene dichloride], which polymer is manufactured and sold by Buckman Laboratories Inc. under the names Busan® 77 and WSCP as a biocide used primarily in aqueous systems. Busan® 77 product is a 60 weight percent aqueous dispersion of the polymer.

The invention also provides a fertilizer composition comprising at least one fertilizer and at least one compound of formula I, defined above. The preferred embodiments of the compound of formula I used in this fertilizer composition are the same as above. In a preferred embodiment, the fertilizer is capable of foliar application. The fertilizer composition may further comprise water. The fertilizer may contain one or more chemical compounds that contain one or more plant nutrients such as nitrogen, phosphorous, potassium, boron, copper, iron, manganese, molybdenum, zinc, or sulfur, in a form capable of fertilizing a plant. Examples of the chemical compounds that may be present in the fertilizer include ammonium, urea, phosphoric anhydride, potassium oxide, boric acid, copper sulfate, iron ethylenediaminetetraacetic acid, manganese ethylenediaminetetraacetic acid, zinc sulfate, sodium molybdate, and sulfates.

The fatty acid residue $R_3C(O)$—, of the compound I of the fertilizer composition, defined above, may be a substituted or unsubstituted residue of a fatty acid which occurs in a vegetable oil. The vegetable oil may be selected from tall oil, palm oil, soybean oil, cottonseed oil, coconut oil, corn oil, peanut oil, canola oil, safflower oil, sunflower oil, babassu oil, castor oil, linseed oil, olive oil, and tung oil. In a preferred embodiment, the vegetable oil may be selected from tall oil, palm oil, and soybean oil.

The invention also encompasses a fertilizer composition, defined above, in which the compound of formula I is present in a modified vegetable oil which forms part of the fertilizer composition. The modified vegetable oil may be selected from modified tall oil, palm oil, soybean oil, cottonseed oil, coconut oil, corn oil, peanut oil, canola oil, safflower oil, sunflower oil, babassu oil, castor oil, linseed oil, olive oil, and tung oil. In a preferred embodiment, the modified vegetable oil is selected from modified tall oil, palm oil, and soybean oil.

Additional embodiments of the invention that increase the effectiveness of a fertilizer may also be utilized. For example, a method of increasing the effectiveness of a fertilizer, preferably capable of foliar application, and concentrated fertilizer formulations may be used in the same manner as for a pesticide.

Specifically, the invention provides a method of increasing the effectiveness of a fertilizer which comprises applying to an exposed portion of a plant in need thereof a fertilizer and an amount of a compound of formula I effective to increase the fertilizing activity of the fertilizer. The definition and preferred embodiments of the compound of formula I as employed in this method are the same as above. In a preferred embodiment, the fertilizer is capable of foliar application. The fertilizer capable of foliar application is preferably applied, along with the compound of formula I, to an exposed portion of the plant. The compound of formula I may be present in a modified vegetable oil. The compound of formula I and the fertilizer may be applied simultaneously or separately. In a preferred embodiment, the compound of formula I and the fertilizer are applied simultaneously in the form of an aqueous solution which comprises both the compound of formula I and the fertilizer.

The method and composition of the invention are applicable to other agronomic crops and to weeds and other types of undesirable plants growing in or along, for example, various types of waterways, highways, or railroad rights-of-way.

The pesticidal concentrated formulations may be diluted in water to form stable suspensions. These stable suspensions may be applied to objects or targets, especially vegetation, using conventional agricultural or pesticidal spray equipment. The pesticidal concentrated formulations may contain other additives known in the art such as surfactants, emulsifiers, dispersants, etc.

In a preferred embodiment, the present invention provides a biologically effective combination of two different types of chemicals, namely, (1) amide or dialkylamide derivatives of vegetable oils, as exemplified by the compound of formula I, defined above, and (2) formulations containing the phytotoxicant endothall (7-oxabicyclo[2,2,1]heptane-2,3-dicarboxylic acid). Vegetable oils are those oils which are derived from various plant parts. Any vegetable oil may be used in the present invention. Common examples of vegetable oils are tall (pine), corn, soybean, cottonseed, palm, and coconut oils. Vegetable oils comprise a variety of saturated and unsaturated fatty acids with different carbon chain lengths and, where unsaturated, different degrees of unsaturation (see Table I).

TABLE I

Principal Saturated (S) and Unsaturated (U)
Fatty Acids in Vegetable Oils

| Fatty Acid | Fatty Acid Carbon Chain Length | | | |
|---|---|---|---|---|
| | 12 | 14 | 16 | 18 |
| Lauric | S | | | |
| Myristic | | S | | |
| Palmitic | | | S | |
| Stearic | | | | S |
| Lauroleic | U | | | |
| Myristoleic | | U | | |
| Palmitoleic | | | U | |
| Oleic | | | | U |
| Linoleic | | | | U |

Table II documents that these oils differ in their average analyses for the types and amounts of specific fatty acids (*Composition and Constants of Fats and Oils*, Armour Chemical Division, Chicago, Ill.).

TABLE II

Percent Composition of Selected
Fatty Acids in Selected Vegetable Oils

| Oil | Fatty Acid | | | |
|---|---|---|---|---|
| | Lauric | Palmitic | Oleic | Linoleic |
| Coconut | 48 | 9 | 6 | 2 |
| Corn | — | 8 | 46 | 42 |
| Cottonseed | — | 21 | 29 | 45 |
| Palm | — | 42 | 43 | 9 |
| Soybean | — | 8 | 28 | 54 |
| Tall | — | 7 | 44 | 37 |

Thus, vegetable oils are similar in that they all comprise fatty acids. However, individual oils may differ in their average composition of specific fatty acids.

The amide of the vegetable oil, as defined above, is prepared by reacting the vegetable oil with an appropriate amine. For example, the dimethylamide of tall oil (DMATO) is prepared by reacting the tall oil fatty acids (TOFA) with dimethylamine ($R_1=R_2$=methyl). Similarly, the dimethylamides have been prepared for soybean oil (DMASO) and for palm oil (DMAPO). In so doing, the dimethylamide of each constituent fatty acid is prepared. The solvent properties of DMATO are superior to those of TOFA. Other advantages of the amides are that they tend to be liquids at room temperature, and they do not form soaps in alkaline systems. The dimethylamide vegetable oils have enhanced solvency and penetrating action relative to the non-derivatized oils.

Generically, the compounds of formula I, defined above, may be prepared by combining the fatty acid and the appropriate amine under elevated temperature and pressure. In the case of DMATO, the TOFA (tall oil fatty acid) fraction (1.0 mole) is mixed with a slight molar excess (1.1 mole) of dimethylamine. In the cases of other vegetable oils (soybean, palm) in which the fatty acids are present as triglycerides (3 fatty acids/triglyceride), 1.0 mole of the oil is mixed with 3.3 moles of the dimethylamine. These mixtures are heated slowly in a closed vessel to 170° C. at a pressure not to exceed 100 p.s.i. The reaction is held at this point for eight hours. Subsequent analyses have shown that this process achieves at least 95 percent amidation of the constituent fatty acids. In the case of DMATO, excess amine is removed in the aqueous phase formed by the water produced in the reaction. Where triglycerides are involved, excess amine is present in the glycerol phase removed after the reaction.

Busperse® 47 product, sold by Buckman Laboratories, Memphis, Tenn., is a nonionic, organic penetrating and dispersing agent. Busperse® 47 product is 90% DMATO and 10% Ipegal® RC-620 product. Ipegal® RC-620 product is an ethoxylated dodecylphenol manufactured by Rhone-Poulenc, Princeton, N.J.

Industrial uses of Busperse® 47 have included: (a) improved boilout of evaporators commonly used in both the sugar as well as the pulp and paper industries; (b) defoaming action and inhibition of corrosion; (c) viscosity depressant for use in formulating high solids coatings in the paint industry; and (d) fatliquoring aid in the leather industry. None of these applications is based in pesticidal uses or agriculture nor does any of these uses involve biologically active substances such as pesticides.

The present invention can provide significant enhancement of the toxicity of pesticides, particularly herbicides such as endothall, by combining the phytotoxicant in the spray solution with effective amounts of amides or dialkylamides of vegetable oils and specific fatty acids. These combinations with the dialkylamide oils, including Busperse® 47 product, are effective and of potentially significant economic benefit to growers and others who use pesticides. The use of Buspersee® 47 product is, as explained in U.S. Ser. No. 07/990,078, filed Dec. 14, 1992, believed to have been heretofore unknown within the pesticidal and agricultural chemical industry and heretofore unknown and unavailable as a product to growers and pesticide applicators. Examples 1, 2, 3, and 4 below utilized Busperse® 47 product as a source of a representative dialkylamide vegetable oil, specifically DMATO.

The following examples describe a series of greenhouse and field trials in which two chemically distinct products (1) endothall and (2) dialkylamides of vegetable oils, each from unrelated industries, were combined to provide a more phytotoxic combination. The examples given describe a series of greenhouse and field trials with cotton plants and potato vines which demonstrate:

(a) the marked enhancement of the phytotoxicity of endothall (as Accelerate®, Des-i-cate®, and Hydrothol® 191/Bulab® 6050 products) by the dialkylamide vegetable oils;

(b) the ineffectiveness of non-derivatized vegetable oils and specific fatty acids in enhancing the phytotoxicity of endothall; and (c) the preparation of stable and effective formulations comprising endothall (Bulab® 6050 product) and several dialkylamide vegetable oils which provide greatly enhanced phytotoxicity.

The following examples are given to illustrate the invention. It should be understood, however, that the invention is not to be limited to the specific conditions or details set forth in these examples.

EXAMPLE 1

Several substances were surveyed alone and in combination with Des-i-cate® product for the potential to enhance the phytotoxicity of endothall. In order to conduct this initial survey, cotton (*Gossypium hirsutum*) seeds were planted in four-inch square plastic pots containing a commercial planting medium. Seedlings were grown under ambient greenhouse conditions. At the time of application, the cotton seedlings had developed two fully expanded true leaves, and the seedlings were thinned to two plants per pot. Chemical treatments were prepared according to the protocol described in Table III. Percent volume-to-volume (% v/v) is defined as the volume of the specific component divided by the total final volume of the solution. For example, a 5% v/v mixture means that the volume of the specific component divided by the total final volume of the solution is 0.05, i.e., 5%. In Table III, "X" is the initial percent volume-to-volume.

TABLE III

| Treatment | Treatment protocol for the foliar application of desiccant candidates to cotton |
|---|---|
| | Initial (X) and Subsequent Application Rates |
| Des-i-cate ® | X (5%), X/2, X/4, X/8, X/16, X/32 |
| Busperse ® 47 | X (0.23%), X/2, X/4 |
| Busperse ® 293 | X (0.23%), X/2, X/4 |
| Busan ® 77 | X (1.25%), X/2, X/4 |
| Des-i-cate ® + Busperse ® 47 | X (5% + 0.23%), X/2, X/4, X/8, X/16, X/32 |
| Des-i-cate ® + Busperse ® 293 | X (5% + 0.23%), X/2, X/4, X/8, X/16, X/32 |
| Des-i-cate ® + Busan ® 77 | X (5% + 1.25%), X/2, X/4, X/8, X/16, X/32 |
| Busperse ® 47 + Busperse ® 293 | X (0.23% + 0.23%), X/2, X/4 |

Bursperse® 293 product is a 30% aqueous solution of hydroxyethylidene diphosphonic acid, which is sold by Buckman Laboratories. Busan® 77 product is a 60% aqueous dispersion of the ionene polymer poly[oxyethylene(dimethyliminio)ethylene(dimethyliminio)ethylene dichloride].

Spraying was accomplished by propelling the aqueous sample with a Chromist® (Gelman Sciences, Inc., Ann Arbor, Mich.) hand-held canister. The application technique was conducted so as to thoroughly wet the surfaces of the leaves and stems. The treated plants were held in the greenhouse for the duration of the test.

Treatments were evaluated one day after application. A subjective scoring system utilized a 0 to 10 scale in which 0 means no effect and 10 means total phytotoxicity. These estimates provide a measure of the gross phytotoxicities due to the treatments. A score of 10 indicates that 100% of the leaf area exhibits damage, i.e., 100% of the leaf area is dry and brown. A score of 5 indicates that approximately 50% of the leaf area exhibits damage. The gross phytotoxicity scores for the initial survey (Table III) are given in Table IV.

TABLE IV

| | Gross phytotoxicity of selected treatments one day after spray application to cotton seedlings. | | | | | |
|---|---|---|---|---|---|---|
| Treatment | X | X/2 | X/4 | X/8 | X/16 | X/32 |
| Des-i-cate ® | 7 | 6 | 4 | 3 | 1 | 0 |
| Busperse ® 47 | 0 | 0 | 0 | — | — | — |
| Busperse ® 293 | 0 | 0 | 0 | — | — | — |
| Busan ® 77 | 0 | 0 | 0 | — | — | — |
| Des-i-cate ® + Busperse ® 47 | 9 | 8 | 4.75 | 3.25 | 1 | 0 |
| Des-i-cate ® + Busperse ® 293 | 6.75 | 6 | 4 | 2.25 | 1 | 0.5 |
| Des-i-cate ® + Busan ® 77 | 9 | 7 | 6 | 1 | 0 | 0 |
| Busperse ® 47 + Busperse ® 293 | 0 | 0 | 0 | — | — | — |

The data in Table IV demonstrate the concentration dependent phytotoxicity of endothall to young cotton seedlings. None of the additives, Busperse® 47, Busperse® 293, or Busan® 77 products, applied alone was phytotoxic at the concentrations tested. Especially at the two highest concentrations, the combination of Des-i-cate®+Busperse® 47 products provided a greater level of necrosis (tissue death/desiccation) than Des-i-cate® product alone. This enhancement was not seen with Busperse® 293 product, but was evident with Busan® 77 product. No interaction of Busperse® 47 and Busperse® 293 products was observed.

EXAMPLE 2

In order to focus more closely on the enhancement of phytotoxicity with the combination of Des-i-cate®+Busperse® 47 products, another greenhouse trial was initiated. In this test only combinations of Des-i-cate® and Busperse® 47 products were studied when applied to potato vines. Vines were propagated vegetatively from non-treated potato tubers (*Solanum tuberosum* cv. Russet Burbank). Tuber slices were planted in six-inch diameter plastic pots containing a commercial planting medium. Vines were grown under ambient greenhouse conditions with occasional watering. Chemical treatments were prepared in which a concentration series of Des-i-cate® product was prepared at each of several concentrations of Busperse® 47 product. The spray applications to the potato vines were conducted as described in Example 1. The treated plants were held in the greenhouse for the duration of the test. Treatments were evaluated five days after application. Gross phytotoxicity scores were determined subjectively as described in Example 1.

TABLE V

| Interaction of Des-i-cate ® and Busperse ® 47 products on Phytotoxicity to Potato Vines | | | | | |
|---|---|---|---|---|---|
| | | Des-i-cate ® (% v/v) | | | |
| | | 0.0 | 0.16 | 0.31 | 0.62 |
| Busperse ® 47 (% v/v) | 0.0 | 0 | 1.0 | 1.2 | 3.8 |
| | 0.31 | 0 | 2.5 | 9.0 | 9.5 |
| | 0.62 | 0 | 8.3 | 9.0 | 9.2 |
| | 1.25 | 0 | 10 | 10 | 10 |

The data in Table V document that Busperse® 47 product was non-phytotoxic to potato vines over the concentration series in the test. In the absence of Busperse® 47 product (0.0 % v/v), Des-i-cate® product provided a relatively low level of phytotoxicity over the concentration range tested. The combination of the two products in one solution prior to spraying dramatically increased the desiccant effect. For example, vines treated with 0.16% Des-i-cate® product alone were given a score of 1.0 on a 1 to 10 scale. However, the potato vines were killed (score=10) when that same level of Des-i-cate® product was combined with Busperse® 47 product at 1.25%.

EXAMPLE 3

To demonstrate the usefulness of the combination of Des-i-cate® plus Busperse® 47 products as a desiccant for field-grown plants, applications were made to standard field production potato vines located at Center, Colo. Des-i-cate® product alone at one concentration, and at three concentrations combined with one level of Busperse® 47 product (3% v/v) was applied by standard spray techniques (equivalent to 20 gallons/acre) to replicated plots of vigorous potato vines (variety Centennial Russet). Applications were conducted late in the growing season when chemical desiccation of vines is standard practice. Evaluations for phytotoxicity were determined separately for leaves and vines two weeks after application. Because each treatment comprised three replicates, the statistical comparison of treatment averages was based on the Duncan's Multiple Range Test. The results appear in Table VI. The pounds of active ingredient per acre is indicated by "# ai/A".

TABLE VI

Effect of Busperse ® 47 product on the Phytotoxicity of Des-i-cate ® product to Field Grown Potato Vines

| Treatment | # ai/A | Percent Desiccation | |
| --- | --- | --- | --- |
| | | Leaves | Vines |
| Control | 0.0 | 0.0 d | 0.0 d |
| Des-i-cate ® | 1.0 | 83.3 b | 65.0 c |
| Des-i-cate ® + Busperse ® 47 (3%) | 0.33 | 71.7 c | 66.7 c |
| Des-i-cate ® + Busperse ® 47 (3%) | 0.66 | 83.3 b | 81.7 b |
| Des-i-cate ® + Busperse ® 47 (3%) | 1.0 | 97.0 a | 93.3 a |

In Table VI the percent values are the average of three replicates. The means within a column followed by the same letter are not significantly different (Duncan's MRT, p=0.05). The data in Table VI demonstrate that Busperse® 47 product is effective in providing a statistically significant increase in the phytotoxicity to potato leaves and vines caused by Des-i-cate® product. With regard to vine desiccation, the combination of Des-i-cate® (0.33 # ai/A)+Busperse® 47 products was as effective as Des-i-cate® product (1.0 # ai/A) alone. For leaves, the combination of Des-i-cate® (0.66 # ai/A) +Busperse® 47 products was as effective as Des-i-cate® product (1.0 # ai/A) alone. The data in Table VI are evidence that a higher degree of vine desiccation may be achieved by adding a relatively low level of Busperse® 47 product and reducing the concentration of Des-i-cate® product. Des-i-cate® product is much more expensive than Busperse® 47 product. In production, growers understandably prefer the most cost effective harvest aid. The data from which Table VI was constructed are presented in Table VII.

TABLE VII

Raw Data for Treatment Replicates in Table VI

| Treatment | # ai/A | | Percent Desiccation | | | |
| --- | --- | --- | --- | --- | --- | --- |
| | | | Rep 1 | Rep 2 | Rep 3 | X̄ |
| Control | 0.0 | Leaves | 0.0 | 0.0 | 0.0 | 0.0 |
| | | Vines | 0.0 | 0.0 | 0.0 | 0.0 |
| Des-i-cate ® | 1.0 | Leaves | 80 | 85 | 85 | 83.3 |
| | | Vines | 65 | 70 | 60 | 65.0 |
| Des-i-cate ® + Busperse ® 47 (3%) | 0.33 | Leaves | 75 | 70 | 70 | 71.7 |
| | | Vines | 65 | 70 | 65 | 66.7 |
| Des-i-cate ® + Busperse ® 47 (3%) | 0.66 | Leaves | 85 | 80 | 85 | 83.3 |
| | | Vines | 80 | 75 | 90 | 81.7 |
| Des-i-cate ® + Busperse ® 47 (3%) | 1.0 | Leaves | 97 | 98 | 96 | 97.0 |
| | | Vines | 95 | 90 | 95 | 93.3 |

EXAMPLE 4

Another example of the enhanced desiccation with Busperse® 47 product was developed using field-grown cotton. Accelerate® product is the endothall-containing product registered and used as a desiccant for cotton. The desiccation and subsequent abscission of cotton leaves is achieved through chemical application. Fallen leaves reduce the potential for trash in the cotton and facilitate the mechanical harvesting of the cotton bolls. Replicated applications with conventional spray equipment were made to late-season field-grown cotton (variety Deltapine 20). Accelerate® product was applied at one rate (4 pints/acre) alone and in combination with Busperse® 47 product (3% v/v). Ten days after application the treatments were evaluated for percent leaf desiccation, percent leaf drop, and drop potential (0=none, 5=very good).

TABLE VIII

Effect of Busperse ® 47 and Accelerate ® products on the Desiccation and Abscission of Leaves of Field-Grown Cotton.

| Treatment | Rate | Percent | | Drop Potential |
| --- | --- | --- | --- | --- |
| | | Desiccation | Drop | |
| Accelerate ® | 4 pts/A | 38.3 | 48.3 | 2.7 |
| Accelerate ® + Busperse ® 47 (3%) | 4 pts/A | 75.0 | 78.3 | 5.0 |

The percent values and scores for drop potential in Table VIII are the means of three replicates. The data clearly demonstrate the marked enhancement of Accelerate® product by Busperse® 47 product in causing field-grown cotton leaves to desiccate and fall. The combination of the two products received a maximum score for drop potential, but the drop potential for Accelerate® alone was only moderate. The data from which Table VIII was constructed are presented in Table IX.

TABLE IX

Raw Data for Treatment Replicates in Table VIII

| Treatment | Rate | Rep | Percent Desiccation | Drop | Drop Potential |
|---|---|---|---|---|---|
| Accelerate ® | 4 pts/A | 1 | 40 | 50 | 3 |
| | | 2 | 45 | 55 | 3 |
| | | 3 | 30 | 40 | 2 |
| | | X̄ = | 38.3 | 48.3 | 2.7 |
| Accelerate ® + Busperse ® 47 (3%) | 4 pts/A | 1 | 75 | 75 | 5 |
| | | 2 | 75 | 80 | 5 |
| | | 3 | 75 | 80 | 5 |
| | | X̄ = | 75 | 78.3 | 5 |

EXAMPLE 5

Another greenhouse experiment was conducted with cotton plants to determine and compare the relative enhancement activity of several substances. These include the dimethylamides of several oils (DMATO, DMASO, and DMAPO), the non-derivatized tall oil fatty acids (TOFA), specific fatty acids (oleic and linoleic), and Ipegal® RC-620 surfactant. Treatments were applied to cotton plants possessing an average of two fully expanded true leaves. A custom made spray booth was utilized which delivered the treatments across the tops of the cotton plants in a controlled and reproducible manner. Pressure regulated (40 psi) applications were made through a standard agricultural nozzle tip (LE-1, 80° nozzle tip, manufactured by Delavan-Delta, Inc., Lexington, Tenn.). In this test, the concentrations of Accelerate® were much below those normally used in agricultural practice due to the small and more sensitive nature of greenhouse-grown plants. The concentrations of the dimethylamide oils and of the Ipegal® RC-620 surfactant are those provided by the 3% level of Busperse® 47 product. Busperse® 47 product is 90% DMATO and 10% Ipegal® RC-620 product. Thus, at a test level of 3% Busperse® 47 product, the concentration of each of the dimethylamide oils is 2.7% by weight (0.90 DMATO×3%=2.7%) and the concentration of Ipegal® RC-260 surfactant is 0.3% (0.10 Ipegal® RC-620 product×3%=0.3%). The levels of oleic and linoleic acids are those which on average would be provided by a 2.7% level of the TOFA fraction. Treated plants were incubated in the greenhouse, and gross phytotoxicity was recorded at one and four days after treatment.

TABLE X

Gross Phytotoxicity of Selected Treatments Applied to Greenhouse Grown Cotton Plants

| Treatment | Rating Day 1 | Day 4 |
|---|---|---|
| Control (water) | 0 | 0 |
| Busperse ® 47 (3% v/v) | 0 | 0 |
| Accelerate ® (0.062% v/v) | 0 | 0 |
| Accelerate ® (0.125%) | 0 | 0 |
| Accelerate ® (0.25%) | 0 | 0 |
| Accelerate ® (0.125%) + Busperse ® 47 | 2 | 3 |
| Accelerate ® (0.125%) + DMATO (2.7%) | 2 | 3 |
| Accelerate ® (0.125%) + DMASO (2.7%) | 2 | 3 |
| Accelerate ® (0.125%) + DMAPO (2.7%) | 2 | 3 |
| Accelerate ® (0.125%) + RC-620 (0.3%) | 0 | 0 |
| Accelerate ® (0.125%) + TOFA (2.7%) | 0 | 0 |
| Accelerate ® (0.125%) + Oleic (1.35%) | 0 | 0 |
| Accelerate ® (0.125%) + Linoleic (1.08%) | 0 | 0 |

The data in Table X demonstrate that none of the three concentrations of Accelerate® was phytotoxic. A non-phytotoxic level of Busperse® 47 product clearly enhanced the phytotoxicity of the endothall product. Furthermore, it is evident that the action of Busperse® 47 product is accounted for by the DMATO contained therein. Equally effective were DMASO and DMAPO. The corresponding level of Ipegal® RC-620 surfactant contained in 3% Busperse® 47 product was ineffective. Also ineffective was the non-derivatized tall oil fatty acids fraction (TOFA, used to prepare DMATO) as well as the individual fatty acids (oleic and linoleic) contained in TOFA.

EXAMPLE 6

Agricultural pesticides are marketed as stable and concentrated formulations which are diluted with water just prior to application in the field. Stable formulations were developed and the effectiveness of these formulations containing endothall plus DMATO, DMASO, or DMAPO was evaluated. The following formulations were prepared:

| Component | Percent (weight/weight) Formulation | | |
|---|---|---|---|
| | D | E | F |
| Bulab ® 6050 | 50 | 50 | 50 |
| DMAPO | 35 | — | — |
| DMASO | — | 35 | — |
| DMATO | — | — | 35 |
| Propylene glycol | 15 | 15 | — |
| Dipropylene glycol | — | — | 15 |
| Total | 100 | 100 | 100 |

Propylene glycol and dipropylene glycol are coupling agents. For comparison, Formulation 1 was prepared as a 50/50 (weight/weight) solution of Bulab® 6050 product plus water. Bulab® 6050 product is a solution of 53 weight percent of mono(N,N-dimethylalkylamine) salts of endothall and 47 weight percent inert ingredients, which are believed to be water and at least one surfactant. Bulab® 6050 product is an amber liquid with a slightly fatty, amine odor, and a density of 1.03 g/ml. It has a boiling point of 88° C. to 98° C., a flash point of 136° F., and a pH of 5.5 to 6.0. Bulab® 6050 product is miscible in water.

It is believed that the mono(N,N-dimethylalkylamine) salts of endothall present in Bulab® 6050 product are derived from coconut oil in the following manner. Starting with coconut oil, the fatty acids are present as a triglyceride, which is three fatty acids hooked to a glycerol backbone. The individual fatty acids are liberated by hydrolysis and removed from the glycerol. The fatty acids are then reacted with dimethylamine in a process which attaches the amine nitrogen to the carboxyl carbon forming the dimethylalkyl amine. The specific alkyl groups involved are those which conform to the fatty acid analysis for coconut oil given in Tables I and II. These alkylamines are then used to form the salt of the endothall in order to make the Bulab® 6050 product.

Formulations D, E, and F remained clear and homogeneous upon standing for one month. The comparison of the phytotoxicity of formulations 1, D, E, and F was conducted in greenhouse experiments on cotton plants as described in Example 5. The spray booth was used to apply an aqueous dilution series of each formulation in a controlled and reproducible manner. The gross phytotoxicity (0 to 10 scale) provided by each treatment was evaluated at one day after application (see Table XI).

TABLE XI

Comparative Phytotoxicities to Cotton of Formulations Containing Endothall Plus DMAPO, DMASO, or DMATO.

| | Percent (v/v) | | |
|---|---|---|---|
| Formulation | 0.25 | 0.5 | 1.0 |
| 1 | 0 | 0 | 1 |
| D | 0 | 1 | 4 |
| E | 0 | 3 | 5 |
| F | 0 | 2 | 5 |

The results in Table XI demonstrate that stable and effective formulations containing endothall (Bulab® 6050) plus DMAPO, DMASO, or DMATO were prepared. Upon dilution with water, Formulations D, E, and F were substantially more phytotoxic than the equivalent concentration of endothall alone (Formulation 1).

EXAMPLE 7

Additional studies were conducted to evaluate formulations and the effective ratios of the principal ingredients, endothall and the dialkylamide vegetable oil. Because the data from Examples 5 and 6 demonstrated that all of the dimethylamide vegetable oils were effective, DMASO was chosen as a representative material with which to proceed. The following formulations were prepared:

| | Percent (weight/weight) Formulation | | |
|---|---|---|---|
| Component | X | Y | Z |
| Bulab ® 6050 (A) | 35 | 35 | 35 |
| DMASO (B) | 50 | 35 | 20 |
| Dipropylene glycol monomethyl ether | 5 | 30 | 45 |
| Atlox ® 8916 TF | 10 | — | — |
| Total | 100 | 100 | 100 |
| A:B | 1:1.4 | 1:1 | 1:0.6 |

Atlox® 8916 TF surfactant is manufactured by ICI, Wilmington, Del. For comparison, Formulation 2 was prepared, which comprised a 35/65 (weight/weight) solution of Bulab® 6050 product/water. Formulations X, Y, and Z remained clear and homogeneous upon standing. The comparison of the phytotoxicity of formulations 2, X, Y, and Z were conducted in greenhouse experiments on cotton plants as described in Example 5. The spray booth again was utilized to apply the treatments to the test plants. The gross phytotoxicity (0 to 10 scale) provided by each treatment was recorded at one and four days after application (see Table XII).

TABLE XII

Comparative Phytotoxicities to Cotton of Formulations Containing Different Ratios of Endothall and DMASO

| | Day 1 | | | | Day 4 | | | |
|---|---|---|---|---|---|---|---|---|
| | Percent (v/v) | | | | | | | |
| Formulation | 0.25 | 0.5 | 1.0 | 1.5 | 0.25 | 0.5 | 1.0 | 1.5 |
| 2 | 0 | 0 | 0 | 1 | 0 | 0 | 0 | 1 |
| X | 1 | 1 | 6 | 8 | 1 | 1 | 7 | 9 |
| Y | 0 | 0 | 3 | 5 | 0 | 0 | 5 | 8 |
| Z | 0 | 0 | 3 | 4 | 0 | 0 | 5 | 6 |

The data in Table XII corroborate those in Table V which indicate that the marked improvements in the phytotoxicity of endothall when combined with the dimethylamide oils may be achieved with varying ratios in which either of the two components may be in excess. When diluted with water, Formulations X, Y, and Z formed suspensions which remained stable throughout the spray application procedure. On both Day 1 and Day 4, these three formulations followed an order of activity (X>Y>Z) in which the relative content of DMASO followed the same sequence. All formulations which incorporated DMASO provided a dramatic increase in phytotoxicity relative to the equivalent concentration of endothall alone (Formulation 2).

These new compositions which greatly increase the phytotoxicity of endothall when foliarly applied have been shown to be of significant benefit in preliminary field studies with potato vines (Example 3) and cotton (Example 4). This invention provides a composition and method for reducing the amount of herbicide applied; this reduction results in a significant cost advantage to growers whose agronomic practices necessitate the use of a harvest aid.

The claimed invention is:

1. A composition comprising at least one desiccant or a salt thereof and at least one compound selected from the group consisting of dimethylamide of tall oil, dimethylamide of soybean oil, and dimethylamide of palm oil, wherein the compound is present in an amount effective to increase the activity of the desiccant wherein said desiccant is endothall or a derivative thereof.

2. The composition of claim 1, wherein the at least one compound is dimethylamide of tall oil.

3. The composition of claim 1, wherein the desiccant is endothall.

4. The composition of claim 1, wherein the compound is dimethylamide of tall oil.

5. The composition of claim 1, wherein the composition further comprises water.

6. A method of increasing the effectiveness of a desiccant or a salt thereof which comprises applying to an object or target a desiccant or a salt thereof and a compound selected from the group consisting of dimethylamide of tall oil, dimethylamide of soybean oil, and dimethylamide of palm oil, wherein the compound is present in an amount effective to increase the activity of the desiccant wherein said desiccant is endothall or a derivative thereof.

7. The method of claim 6, wherein the desiccant and the compound are applied simultaneously.

8. The method of claim 6, wherein the desiccant and the compound are applied together as an aqueous solution.

9. The method of claim 6, wherein the compound is dimethylamide of tall oil.

10. The method of claim 6, wherein the desiccant is endothall.

* * * * *